(12) United States Patent
Krishnan et al.

(10) Patent No.: US 9,326,685 B2
(45) Date of Patent: May 3, 2016

(54) DEVICE FOR EVALUATING CONDITION OF SKIN OR HAIR

(75) Inventors: Srinivasan Krishnan, Stamford, CT (US); Jamie Gordon Nichol, Arlington, MA (US)

(73) Assignee: Conopco, Inc., Englewood Cliffs, NJ (US)

( * ) Notice: Subject to any disclaimer, the term of this patent is extended or adjusted under 35 U.S.C. 154(b) by 842 days.

(21) Appl. No.: 13/617,098

(22) Filed: Sep. 14, 2012

(65) Prior Publication Data

US 2014/0081095 A1 Mar. 20, 2014

(51) Int. Cl.
*A61B 5/00* (2006.01)
*A61B 5/053* (2006.01)

(52) U.S. Cl.
CPC .............. *A61B 5/0059* (2013.01); *A61B 5/0077* (2013.01); *A61B 5/0531* (2013.01); *A61B 5/443* (2013.01); *A61B 5/448* (2013.01)

(58) Field of Classification Search
CPC .... A61B 5/0059; A61B 5/448; A61B 5/0531; A61B 5/443; A61B 5/0077
USPC ........................................ 600/306
See application file for complete search history.

(56) References Cited

U.S. PATENT DOCUMENTS

| | | |
|---|---|---|
| 4,013,065 A | 3/1977 | Copeland et al. |
| 4,398,541 A | 8/1983 | Pugliese |
| 4,711,244 A | 12/1987 | Kuzara |
| 4,860,753 A | 8/1989 | Amerena |
| 5,001,436 A | 3/1991 | Scot |
| 5,226,431 A | 7/1993 | Bible |
| 5,622,692 A | 4/1997 | Rigg |
| 5,938,593 A | 8/1999 | Ouellette |
| 5,945,112 A | 8/1999 | Flynn |
| 6,529,767 B1 | 3/2003 | Woo |
| 6,628,724 B2 | 9/2003 | Bannasch |
| 7,090,649 B2 | 8/2006 | Kang |
| 7,547,280 B2 | 6/2009 | Yanagihara |
| 2002/0065452 A1 | 5/2002 | Bazin et al. |
| 2002/0183624 A1* | 12/2002 | Rowe et al. .................. 600/476 |
| 2003/0065523 A1 | 4/2003 | Pruche |

(Continued)

FOREIGN PATENT DOCUMENTS

| | | |
|---|---|---|
| CA | 2376747 A1 | 9/2003 |
| CN | 100346743 | 11/2007 |

(Continued)

OTHER PUBLICATIONS

PCT International Search Report and Written Opinion on Application No. PCT/EP2013/067705 dated Dec. 5, 2013.

(Continued)

*Primary Examiner* — Michael Kahelin
*Assistant Examiner* — Tho Tran
(74) *Attorney, Agent, or Firm* — Greenberg Traurig, LLP

(57) ABSTRACT

The present invention relates to a device for evaluating condition on skin or hair. The device provides one extension supporting a hydration meter suitable for measuring hydration values in areas difficult to measure (e.g., skin in scalp area) and; a separate extension supporting a camera for capturing images of an area of skin or hair and transferring said image to computer. Data from these sources are evaluated and scored. The multiple data points are used to provide a highly targeted product best suited for each individual consumer.

17 Claims, 6 Drawing Sheets

(56) References Cited

U.S. PATENT DOCUMENTS

| | | |
|---|---|---|
| 2003/0149347 A1 | 8/2003 | Kauffmann |
| 2003/0214311 A1 | 11/2003 | Alanen |
| 2004/0073081 A1 | 4/2004 | Schramm |
| 2004/0086456 A1 | 5/2004 | Shirai |
| 2004/0171962 A1 | 9/2004 | Leveque et al. |
| 2005/0101250 A1 | 5/2005 | Helal |
| 2005/0159655 A1 | 7/2005 | Kao |
| 2007/0056859 A1 | 3/2007 | Sherman |
| 2007/0060819 A1 | 3/2007 | Altshuler et al. |
| 2007/0185392 A1 | 8/2007 | Sherman et al. |
| 2008/0012582 A1 | 1/2008 | Jang |
| 2008/0045816 A1 | 2/2008 | Jang |
| 2008/0177198 A1 | 7/2008 | Jang |
| 2008/0194928 A1* | 8/2008 | Bandic et al. ............ 600/306 |
| 2008/0221411 A1 | 9/2008 | Hausmann et al. |
| 2008/0259322 A1 | 10/2008 | Korotkov |
| 2009/0009193 A1 | 1/2009 | Hsiung |
| 2009/0076639 A1 | 3/2009 | Pak |
| 2009/0112071 A1 | 4/2009 | LeBoeuf et al. |
| 2009/0143653 A1* | 6/2009 | Laurens et al. ............ 600/306 |
| 2009/0318908 A1 | 12/2009 | Van Pieterson et al. |
| 2012/0041282 A1 | 2/2012 | Nichol |
| 2012/0041283 A1 | 2/2012 | Krishnan et al. |
| 2012/0041284 A1 | 2/2012 | Krishnan et al. |
| 2013/0123587 A1* | 5/2013 | Sarrafzadeh et al. ......... 600/306 |

FOREIGN PATENT DOCUMENTS

| | | |
|---|---|---|
| DE | 4405624 A | 8/1995 |
| GB | 2136575 | 9/1984 |
| JP | 60198449 | 10/1985 |
| JP | 4377135 | 12/1992 |
| JP | 5146412 | 6/1993 |
| JP | 2001198091 | 7/2001 |
| JP | 2001330780 | 11/2001 |
| JP | 2003210416 | 7/2003 |
| JP | 2003210416 A | 7/2003 |
| JP | 2003210416ABS A | 7/2003 |
| JP | 2003256561 | 9/2003 |
| JP | 200433727 | 2/2004 |
| JP | 2004187248 | 7/2004 |
| JP | 2005152401 | 6/2005 |
| JP | 2006296816 | 11/2006 |
| JP | 2010004903 | 1/2010 |
| KR | 960006662 B | 5/1996 |
| KR | 20060114881 | 11/2006 |
| KR | 1020090131370 | 12/2009 |
| RU | 2232473 | 7/2004 |
| SE | 435424 | 9/1984 |
| WO | WO2008064120 A2 | 5/2008 |
| WO | WO2008109421 | 9/2008 |
| WO | WO2010049907 A2 | 5/2010 |
| WO | WO2010049907 A2 | 5/2010 |

OTHER PUBLICATIONS

IPRP1 in PCTEP2013067705 dated Mar. 17, 2015. In J9217US-NPLRef, pp. 1 to 7.
IPRP2 in PCTEP2011057938 dated Oct. 1, 2012. In J9217US-NPLRef, pp. 8 to 14.
IPRP2 in PCTEP2011059995 dated Oct. 15, 2012. In J9217US-NPLRef, pp. 15 to 20.
IPRP2 in PCTEP2011063744 dated Dec. 20, 2012. In J9217US-NPLRef, pp. 21 to 42.
Search Report in PCTEP2011057938 dated Jul. 22, 2011. In J9217US-NPLRef, pp. 43 to 45.
Written Opinion in PCTEP2011057938 dated Jul. 22, 2011. In J9217US-NPLRef, pp. 46 to 51.
Search Report in CN201180049506, May 19, 2014 (translation).
Hashimoto-Kumasaka et al., Electrical measurement of the water content of the statrum conreum in vivo and in vitro under various conditions: comparison between skin surface hygrometer and corneometer in evalatuion of the skin surface hydration state, Acta Derm Venereol, Oct. 1993, vol. 73, No. 5, pp. 335-359.
Hester et al., Evaluation of Corneometry (Skin Hydration) and Transepidermal Water-Loss Measurements in Two Canine Breeds, The American Society for Nutritional Sciences, 2004, vol. 134, pp. 2110S-2113S.
Co-pending Application: Applicant: Krishnan et al., U.S. Appl. No. 12/855,728, filed Aug. 13, 2010.
PCT International Search Report in PCT application PCT/EP2011/059995 dated Sep. 2, 2011 with Written Opinion.
Co-pending Application: Applicant: Nichol et al., U.S. Appl. No. 12/855,727, filed Aug. 13, 2010.
PCT International Search Report in PCT application PCT/EP2011/063744 dated Nov. 4, 2011 with Written Opinion.
Co-pending Application: Applicant: Krishnan et al., U.S. Appl. No. 29/432,276, filed Sep. 14, 2012.
Co-pending Application: Applicant: Krishnan et al., U.S. Appl. No. 29/432,283, filed Sep. 14, 2012.
Co-pending Application: Applicant: Krishnan et al., U.S. Appl. No. 29/432,279, filed Sep. 14, 2012.

* cited by examiner

DEVICE FOR EVALUATING CONDITION OF SKIN OR HAIR

FIELD OF THE INVENTION

The present invention relates to a novel device for evaluating (e.g., measurements relating to) skin or hair condition. The device may be used to measure hydration values of skin, particularly on areas where it is difficult to evaluate and obtain such measurements, e.g. the skin on the scalp. The device comprises a camera, attached to a prong or extension of the device separate from the prong containing the hydration sensor. The camera captures images of the measurement areas and these images are used in conjunction with the measurement of hydration values to evaluate skin or scalp problems and help recommend products to ameliorate skin or scalp condition.

The invention also comprises a method for evaluating skin on the scalp and recommending product for ameliorating skin or scalp conditions which method comprises (1) applying one prong of a device containing hydration meter or sensor to the scalp (i.e., skin on a part in the hair on the scalp) to obtain hydration measurement values; (2) using camera located on separate prong of the same device to capture images for additional evaluation, which evaluation may be used separately or in conjunction with hydration measurements; and (3) utilizing hydration values and images obtained in computer program either separately or together to provide a product recommendation.

BACKGROUND OF THE INVENTION

Most people have skin or hair imperfections. The cosmetic impact of hair and skin imperfections can be ameliorated with the use of an appropriate product. Selection of appropriate product for any given individual begins with an evaluation of the person's skin or hair (skin of the scalp can be used for such an evaluation).

Although various methods for measuring properties of skin or hair may be known, measurement can be more difficult to obtain on same parts of the body than on others. Thus, for example, it is not difficult to apply a hydration measurement device to areas of the body such as arms or cheeks because there is generally far less interference from hairs. Further, such areas generally offer a very shallow curvature and are compliant, readily conforming to the sensing surface of the hydration measurement device with little force. However, it is often a challenge to apply such devices to the skin in the scalp area because of interference from hair. That is, hair can be trapped between a sensor and the skin of the scalp, for example. Hair entrapment reduces contact between the skin of the scalp and the sensor resulting in an erroneous hydration measurement. Also, the contour of the scalp is such that a conventional hydration sensor cannot be readily applied due to curvature of the scalp as well as the relative non-compliance of the scalp and underlying tissue. This non-contact and excessive force when taking a hydration measurement also introduce error.

In the recommendation of appropriate hair care products in particular, it would be highly beneficial to obtain evaluation and measurements (e.g., hydration value measurements) from the skin of the scalp area. For example, a person who has imperfections of the skin of the scalp (e.g., exhibiting skin dryness, redness, dandruff) often requires different product from a person having skin of the scalp in generally good condition. However, it is not easy to obtain measurements readily on skin of the scalp both because of the contours of the head as well as interference of hair follicles typically present there. That is, hair trapped between the active surface of the hydration measurement device and the skin of the scalp alters hydration measurements as noted above.

Applicants have now devised a device comprising a central housing, a hydration meter (sensor) supported within the housing and projecting from at least one side of the housing, the end of which hydration meter has a surface evaluation area whose external surface has an aspect ratio wherein the width is greater than the length (>1:1), defining, for example, a rectangle. Preferably, ratio of width to length is >1.3:1, more preferably ≥2:1 and more preferably ≥3:1. While there is no clear upper limit, higher aspect ratios have small active area for the length, and the curvature of the scalp can become more problematic for long sensors (e.g., because the ends don't touch the skin and don't participate in the measurement which can show that result). Generally, it is desirable to have a sensor length that allows the edges of the sensor to touch the scalp without applying so much force to the skin of the scalp that the force alters the fluid distribution in the skin and skews the measurement. Assuming a rigid sensor (which is not necessarily the case), sensors should preferably be no longer than about 1.3 cm, preferably no longer than 1.2 cm. A more flexible/compliant sensor could be a bit longer (narrower). A narrower sensor is also more favorable (whether using rigid or flexible sensor) because it is less influenced by hair.

The external surface may also be in the form of an ellipse (i.e., wherein the aspect ratio of major axis, i.e., the width, to minor axis i.e., the height, is again >1:1, preferably >1.3:1, more preferably ≥2:1 and more preferably ≥3:1). Indeed, as long as the width is greater than the length or the height, the shape can be rectangular, elliptical, obround, trapezoidal or any shape meeting such definition. As noted above, sensor (especially rigid sensor) should ideally be no longer than about 1.3 cm.

Preferably, the shape is what we refer to as oblong. By oblong can be meant, for example, purely rectangular (straight edges on all sides); or rectangular, but with side edges which define the length/height rounded outward rather than straight, a term we define as obround (see FIG. 6). Such oblong-shape external surface or shape (e.g., obround) has been found particularly suitable for pressing the surface evaluation area of the hydration meter against the skin of the scalp to make optimal contact with skin (e.g., it conforms readily to the curvature of the skull) and most readily obtain hydration values. Further, because camera and sensor need not be co-located (co-location drives conformity with camera lens which lens, for example, is typically circular), such preferred oblong shape can be readily used.

The housing on the device also comprises an electrical wire or optical cord, particularly a USB cable terminating in a USB port which plugs into a computer and accesses programs. The program, for example, makes comparisons of pictures taken by the camera on the device to pictures stored in the program, and/or to stored information gathered relating to hydration values. This is described in further detail below.

Finally, in addition to the hydration meter or sensor (which itself comprises a transducer which changes its electrical capacitance depending on skin hydration; and an interface circuit that measures changes in capacitance and thereby hydration) supported by and projecting from at least one end of a housing (as indicated, the end of said meter terminates in an evaluation area with aspect ratio where width is greater than length or height and is shaped for best contacting skin along the curvature of the scalp); and to a cable terminating in a USB port or other means for transmitting data; the housing further contains a camera (also supported by and projecting from a separate end on the same housing) for capturing and electronically recording images of an area of skin or hair. The captured image is compared (either in software via digital means or by a person) to other images stored in the computer and, based on both an evaluation of computer images done by the computer program and/or evaluation of measured hydration values (or both), the consumer is advised about the state of the scalp so that a preferred cosmetic product can be recommended.

Thus, the device of the invention comprises a housing with (1) one end terminating in a hydration meter or sensor (comprising transducer and interface circuit for picking up and measuring hydration) having surface evaluation area with defined aspect ratio; (2) a separate second end comprising a camera and (3) a separate end terminating in a USB port or other means for transmitting data. Applicant is thus able to effectively measure multiple parameters (e.g., hydration measurement, captured images) to help quantify or define skin (especially skin of the scalp area) or hair condition. Use of multiple parameters (although each can be used alone) makes recommendation of a product highly tailored, targeted and effective.

Applicant has filed an application on a previous device comprising a housing with a hydration meter and a plurality of light emitting diodes. However, the present device is an improvement over that device in several respects. First, based on the shape of the external evaluation surface of the hydration meter, the meter can be readily and easily applied to the contours of the scalp. Further, the hydration meter and camera for capturing images on the scalp are placed on separate extensions of the same device allowing for optimal performance of the hydration meter and camera. As noted above, the separation of the camera and sensor permits use of, for example, an oblong sensor because the sensor need not conform to shape of camera opening. This, in turn, allows sensor to be placed more readily along the curvature of the scalp and to provide more accurate hydration measurements.

SUMMARY OF THE INVENTION

The present invention comprises:

A device for evaluating skin (particularly skin scalp area) condition and/or hair condition which comprises:
  a) a housing;
  b) a hydration meter for measuring moisture or hydration value (comprising a transducer and interface circuit for picking up and measuring hydration) supported by and projecting from at least one end of the housing, the end of which hydration meter has a surface evaluation area (external or outward and designed to be applied to skin or hair) whose external surface may be e.g., rectangular or elliptical but is characterized by having aspect ratio with width greater than length or height. Said shape is particularly suited for contact against the curvature of the scalp;
  c) a camera supported within the housing and projecting from at least a second end (e.g., preferably, there is a light diffuser at the end which optimizes camera image); preferably the camera is in communication with a printer circuit board also found in the device which can relay information gathered by the device to an external computer; and
  d) one end (separate from end comprising hydration meter or end with camera) comprising an electrical wire, cord (e.g., cable) terminating in a USB port (or other means for connecting to a computer). Preferably, the port is connected with computer which obtains information from hydration meter and camera and helps provide final evaluation and recommendation.

As noted, the camera captures and electronically records images of an area of skin or hair. The captured images are transferred to a computer, preferably via a USB cable, and are compared to other images stored in the computer (using a computer and computer program associated with the device) so that the computer program evaluates the captured image compared to the stored image and can convey a "score" or evaluation. Together, the hydration value measured by the hydration meter or sensor, and the camera images, can be used in connection with a recommendation of which product the consumer can obtain. Of course, either may be used alone but, together, these multiple parameters help provide a particularly tailored recommendation.

The invention further comprises a method of optimizing evaluation, and communicating (recommending) to the consumer which product to purchase which method comprises:
  a) applying the hydration measuring device noted above (i.e., the end projecting from housing which comprises the hydration meter pick-up device) to the skin, particularly to the skin along the curvature of the scalp; and
  b) using camera in separate projection of same device to capture images and transfer to computer for evaluation; and
  c) based on hydration value measurement (which can be stored and analyzed by computer) and computer evaluation of images (together, or either independently), suggesting appropriate product to the consumer.

Computer evaluation of skin and/or and recommendation of product based on data from hydration meter on device can be used for consumer evaluation and/or recommendation of product. Computer evaluation of skin and/or hair based on data captured on camera in device can be used for consumer evaluation and/or recommendation of product. Computer evaluation of skin and/or hair based on data from both hydration meter and camera on device can be used for consumer evaluation and/or recommendation.

DETAILED DESCRIPTION OF THE INVENTION

Figure 1:
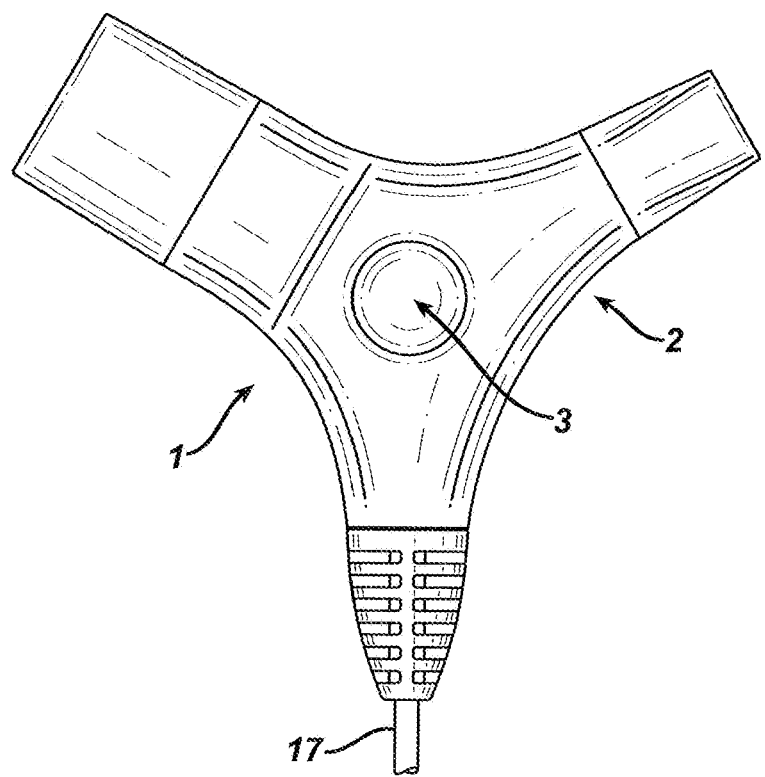
FIG. 1 is a perspective view of the device comprising (1) one projection supporting camera, (2) one projection supporting hydration meter terminating in surface evaluation area (oblong shape in the figures) at distal end and (3) an optical wire or electronic cable 17 with USB port for connecting to computer.

The present invention relates to a device which evaluates the condition of skin, particularly skin on or about the scalp, and/or evaluates condition of hair. It further relates to a method of evaluating the skin (e.g., skin in the scalp area) and recommending product which comprises (a) applying hydration meter on one extension of said device to obtain hydration values; (2) using camera on second extension of same device to capture images which will be compared in a computer; and (3) utilizing both values combined (although each an be used separately) to provide recommendation for hair product.

The device of the invention measures multiple parameters, e.g., relating to measurement of hydration values as well as to capture and recordation of images. Hydration values can be stored and evaluated (e.g., using computer); and camera images are analyzed by a computer programmed to compare images to other pre-programmed images in order to set forth an evaluation based on such image comparison. The data from both sources can be used separately or together.

The device requires (1) a housing; (2) a hydration meter (for picking up and measuring hydration values) supported by and projecting from at least one end of the housing, the end of which hydration meter has a surface evaluation area which has defined aspect ratio (defining for example, a preferred oblong shape), and is particularly suited for contact with the skin along the curvature of the scalp; (3) a camera supported by and projecting from a separate end of the same housing (there is preferably a light diffuser at the terminal end of the projection through which camera points); there is preferably a ring with light emitting diodes attached to broad end of the light diffuser (a narrow end of diffuser being closer to the opening on the housing) and (4) one end comprising an electrical wire terminating in a USB port or similar means for connecting to computer.

The hydration meter measures hydration value which can be recorded in a computer. The camera captures and electronically records images of an area of the skin (especially along the scalp) or hair. The images are transferred to a computer associated with the device and a computer program is used to evaluate the captured image compared to other images stored in the program so that a "score" can be determined.

Use of housing with a hydration meter having an external surface which is particularly suitable for efficient contact with skin along the curvature scalp is a great advancement because it permits far more accurate measurement of hydration. When further combined with use of camera on a separate extension of the same device, the device provides a powerful and efficient way to evaluate and provide to the consumer a recommendation for a product ideally suited for their particular skin/hair.

The device thus combines both a hydration meter (with end ideally suitable for contact with scalp) and a camera operating in tandem via a device having a common data communication port. Data obtained from either the meter, the camera or, preferably both, can be used (using computer which stores and/or compares information) to evaluate skin or hair condition and recommends best suited product to consumer.

It is noted the device is a portable device which can be used at point of sale and is thus of great flexibility.

FIG. 1 illustrates a perspective view of the hand-held device. By the term "hand-holdable" or "hand-held" is meant a device typically measuring in length less than 35 centimeters (cm), preferably between 10 and 25 cm (not including cord) and a width between 2 and 8 cm, preferably between 3 and 6 cm. The device features a housing 1 with a shell 2. Preferably, the shell has a gripping portion which can be as simple as an indentation or depression for the thumb as noted by 3. Normally, the shell is formed of a relatively hard plastic such as ABS (polyacrylonitrile-butadiene-styrene) which is a high impact resistant plastic. Gripping area 3 can be formed of a less rigid material such as rubber.

Figure 2:
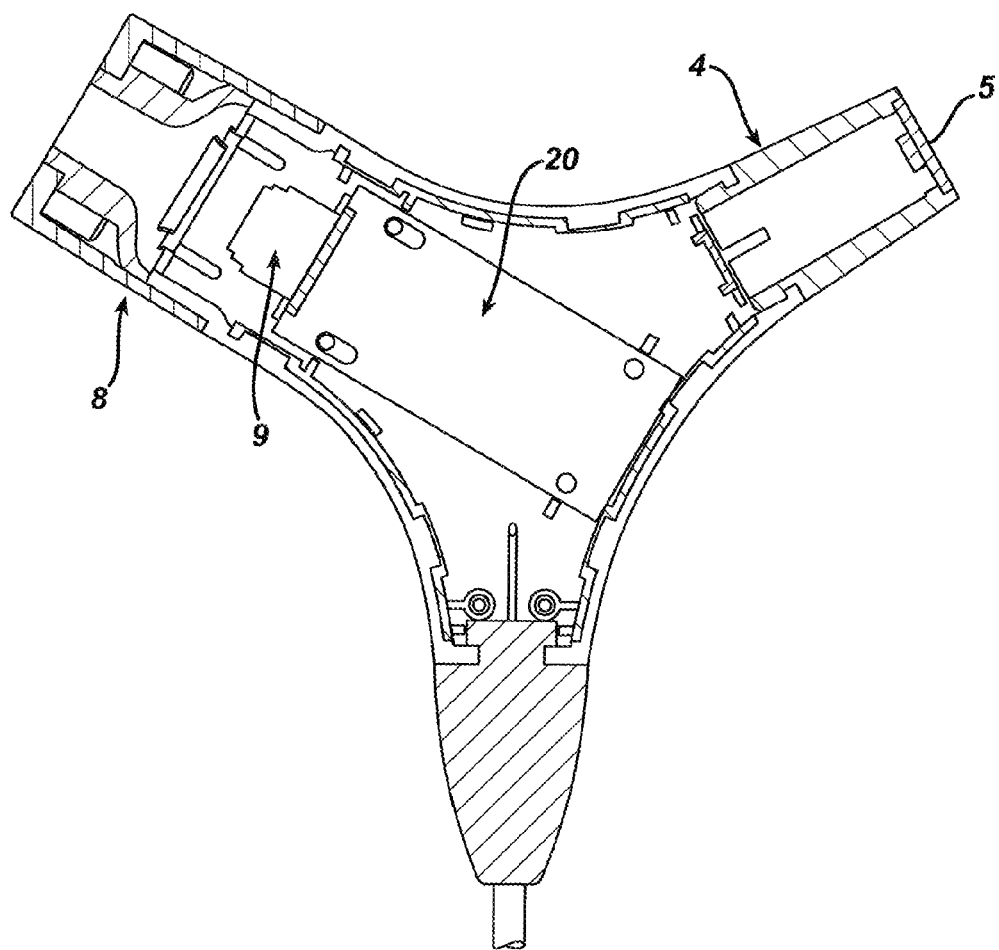
FIG. 2 is a view of the device with the half housing removed. In this figure, camera is at end of a printed circuit board (PCB) found in the middle and lens points outwardly. In this figure there is also a diffuser at distal end of protrusion which ensures optimal picture is taken by camera. As seen more clearly in FIG. 4, 9 represents the lens; and 10, the shaded portion of the PCB (20) where the lens attaches, is the camera chip.

The hydration meter is supported by and projects from the housing; and measurements are taken from surface evaluation area 5 (see FIG. 2). Referring to FIG. 2, the hydration meter projects from housing and terminates in external evaluation area 5 which is obround in shape (see FIG. 6 for greater detail). By obround, we mean that the sides (the length of the rectangle) of what would be a classically shaped rectangle form rounded ends bulging outward rather than forming a straight line from the top to the bottom.

Figure 6:
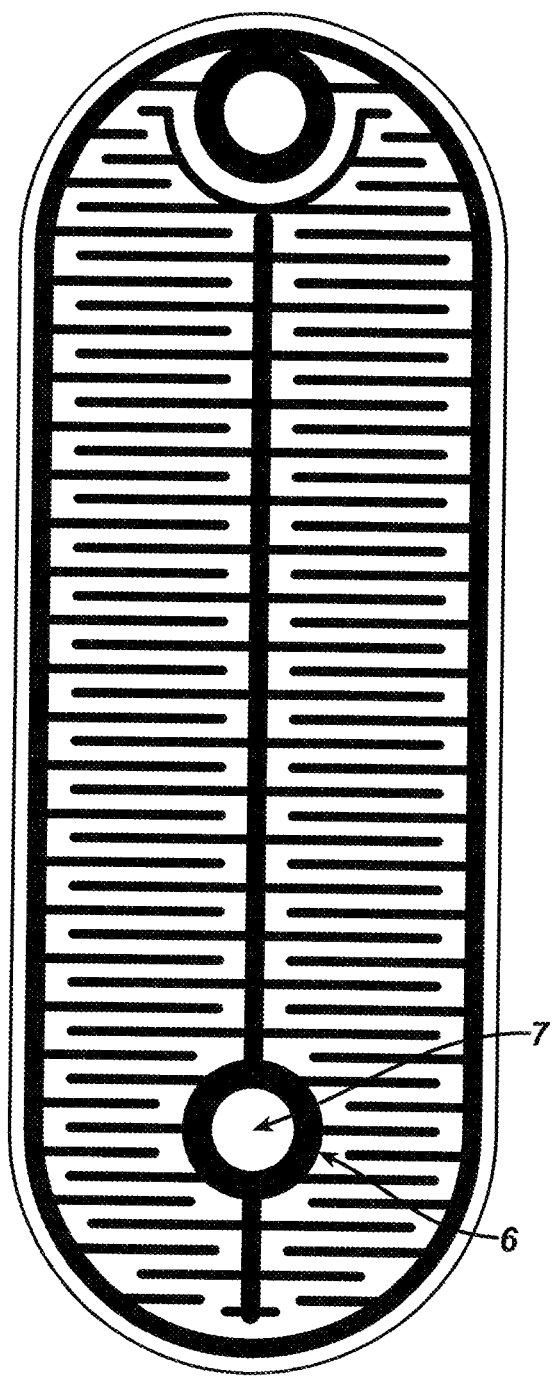
FIG. 6 is a view of an oblong shaped rectangle with circular edges (obround) which is found at the surface of hydration meter and can be applied to skin at, for example, the scalp.

When the external evaluation area 5 is contacted against skin, the first contact surface is a moisture sensing cell 6 seen in FIG. 6. The sensing cell picks up electrical signals from the stratum corneum of skin. Metallic electrical conducting wires, preferably of copper on a circuit board, are typically embedded within a hardened resin of the sensing cell. These wires are sensitive to differences in dielectric constant of their aqueous environment. Differences in relative electrical capacitance resulting from differences in the dielectric constant reveal the measure of moisture at the skin or hair surface. Hydration meters are commercially available from Courage-Khazaka Electronics, Koln, Germany.

More specifically, the sensor is a transducer which is electrically capacitive. The capacitance of the transducer/sensor changes with the hydration of the outer layers of the skin, with which it is brought into contact. Typically, the capacitance (i.e., ability to store electrical charge) of the pick-up is relatively small. A second part of the sensor is an interface circuit that measures this capacitance by repeatedly storing charge in the transducer and shuttling that charge to a larger reference capacitor. The number of times the sensor is discharged into the reference capacitor before the reference capacitor reaches a pre-determined voltage is the hydration measurement.

The evaluation area 5 of the sensor in FIG. 2 is, as noted, shaped to ensure the best contact with scalp skin along the contour of the scalp. Specifically, the area can be rectangular with classic rectangle side or with side length bulging outward as described above and seen in FIG. 6 (obround).

FIG. 2, as noted, is a view with half of the housing removed. The housing can be a pair of separately molded plastic shells. The shells may be fastened together, for example, by alternating male and female peg/socket clasps, arranged along a periphery of the shells. Also present are a male and female pair of wall joints near a rear end of the housing. These wall joints project inward to engage their respective joints on each of the half shells.

Figure 4:
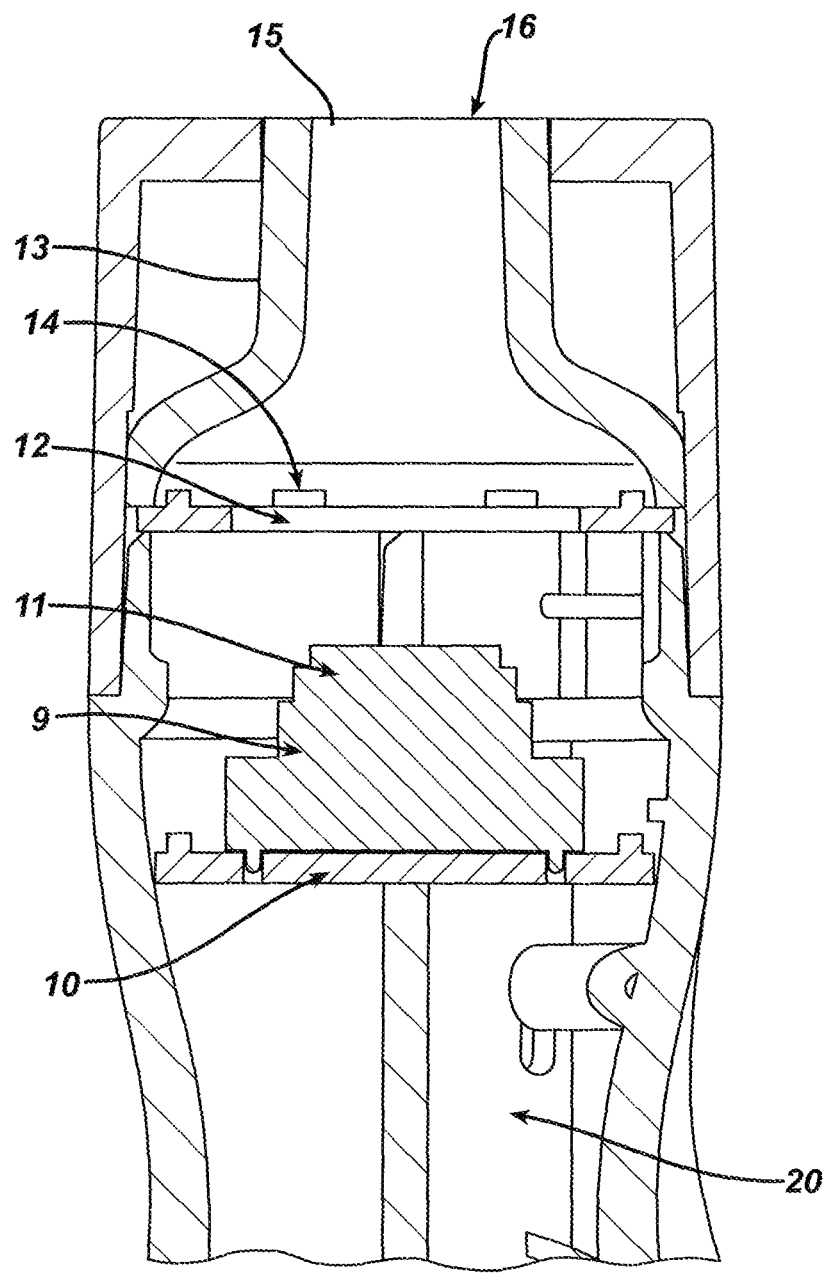
FIG. 4 is view showing camera pointing through diffuser and also showing ring 12 with light emitting diodes 14, wherein the ring is attached to the broad opening of the light diffuser (further away from the opening in the housing).

In FIG. 2, we can also see a separate projection 8 (i.e., separate from projection 4 comprising hydration meter) which comprises a camera 9. The camera 9 is mounted within the housing. As seen in FIG. 4, components of the camera 9 include a camera microchip 10 (attached to PCB 20), a lens system 11, and a diffuser 13. The camera microchip 10 can adjust the lens system, store image information and transmit the images to a receiver outside the housing.

Figure 5:
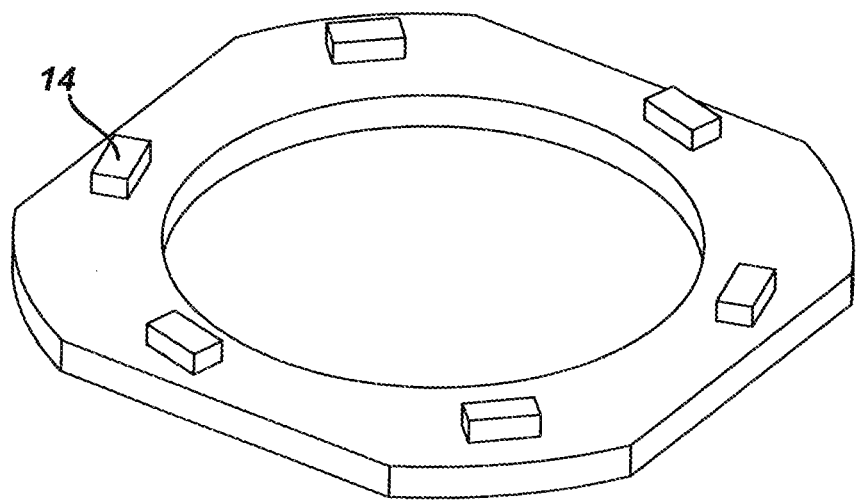
FIG. 5 is view of the ring with light emitting diode.

As further seen in FIG. 4, one or more light emitting diodes (LED) 14 are positioned on the side of ring 12 (also seen in FIG. 5) facing diffuser 13 towards the opening of housing 15. Alternatively, no diffuser may be present. The LED may be any wavelength of light including but not limited to blue wavelength light emitter, infrared wavelength light emitter, white wavelength light emitter etc. or combinations thereof. The LED may be all white LEDs.

Although LED 14 are oriented to emit light downward to opening 15, their light will be intercepted by the funnel-shaped wall segment of diffuser 13. As a consequence, LED emitted light will scatter back and forth along the diffuser and down the tunnel to finally exit through the central transparent window 16 located at opening 15 at the front end of the housing (all part of projection 8 which supports the camera).

Figure 3:
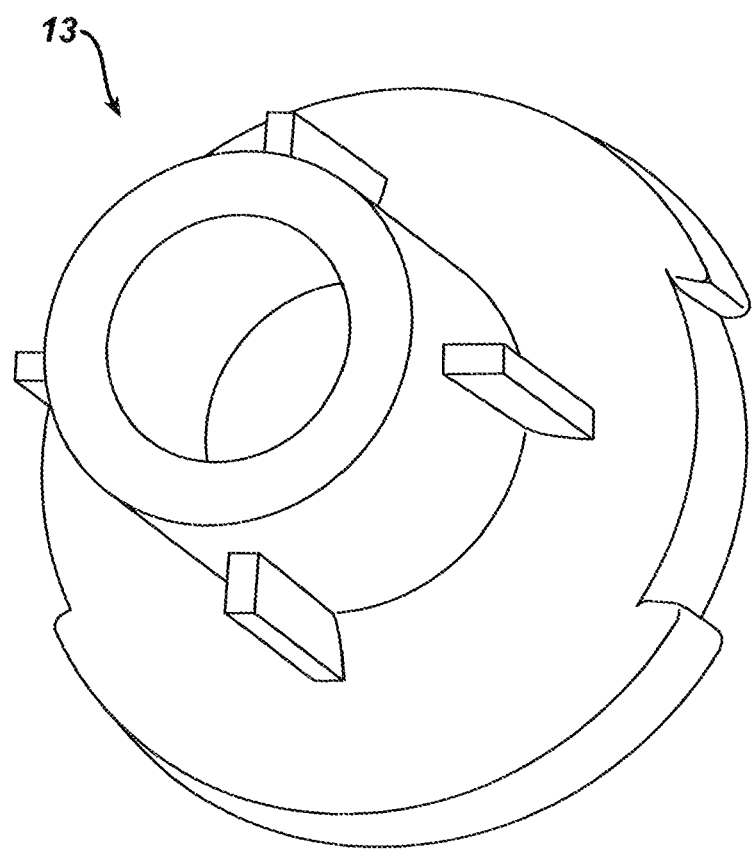
FIG. 3 is blow-up view of light diffuser.

FIG. 3 is a blow-up of the diffuser. All elements of the device can be combined with no diffuser 13 present, although images provided would be of sub-optimal definition.

Data generated from the hydration meter 4 (hydration values) and the LEDs 14 (for camera) initially is in analog form. This form arises because the meter and LEDs are both transducers which inherently provide an analog response to the physical event being measured. The analog data is next converted to digital values (numbers stored in a micro-controller). Thereafter, the digital values are transformed back into analog mode, this time as an audio wave signal. The audio signal is thereafter transformed back into a digital signal at a downstream USB microchip. By this manner we can double the base frequency or reduce the base frequency by half. In summary, the data is converted from analog to digital to analog to digital. This ADAD conversion is a key factor allowing use of off-the-shelf components to transfer skin data in a way the computer already recognizes.

The generated data is converted through a pre-set series of calculations to identify an Index unique to the measured area. The Index permits a user to monitor their skin over a period of time. A product recommended by the program to adjust the consumer's skin into an improved condition may be applied over the monitored period. This allows a consumer to evaluate effectiveness of the product or any other products that might be applied to improve the skin condition.

A USB port (or similar means for transmitting data) is attached to an end of an electrical wire or optical fiber cord 17 as shown in FIG. 1. The USB port can plug into a computer to access a program companion to the device and is the most advantageous connector to the computer. However, the system may also work by Bluetooth or wireless connectivity or serial port connection routes.

Most preferred is that power to the system be delivered externally from an electric grid. Alternatively, power can be supplied by a rechargeable battery or disposable batteries within the device. In circumstances wherein power is supplied by a rechargeable or a disposable battery, the only cord projecting from the housing is the data cord 17.

In one regard, the device can be considered as a "personal trainer" for a user's skin.

A polarizer plate may be placed in tandem with the central window 16. All emitted light will pass through the polarizer plate. With the polarizer, the camera better images wrinkles and spots.

All documents referred to herein, including all patents, patent applications, and printed publications, are hereby incorporated by reference in their entirety in this disclosure.

The invention additionally provides a method for optimizing evaluation of skin (especially measured along the scalp) or hair and for recommending product for treatment. The method comprises (1) applying one prong or extension of the device which contains hydration meter to obtain hydration values; (2) using camera on separate extension of the same device to capture image for additional evaluation when used in conjunction with the hydration measurement (although data of hydration values and data from consumers may be used independently); and (3) using hydration values and/or images obtained in composition program to provide recommended product.

The recommendation can be used based on hydration value data above; based on data from captured camera images done; or based on two together.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above. The term "consisting essentially of", if used, should be understood to mean that, although it may contain other elements or components, these do not materially affect the function of the combination or composition.

Except in the operating and comparative examples, or where otherwise explicitly indicated, all numbers in this description indicating amounts of material ought to be understood as modified by the word "about".

It should be noted that in specifying any range or amount, any particular upper value can be associated with any particular lower value or amount.

The foregoing description illustrates selected embodiments of the present invention and in light thereof variations and modifications will be suggested to one skilled in the art all of which are within the spirit and purview of this invention.

EXAMPLES

Example 1

In order to show whether it would be more effective to use a sensor having an evaluation area where external surface is obround (e.g., rectangular with side edges rounded) in shape, applicants measured hydration values (arbitrary units) using a sensor with obround shape compared to sensor with circular shapes. The measurements were taken on scalp with the hair parted to make space for measurement of hydration.

Data is set forth in Table below:

| Shape | Hydration |
|---|---|
| Round | 336 |
| Round | 574 |
| Round | 813 |
| Round | 1050 |
| Round | 1050 |
| Round | 1050 |
| Round | 1194 |
| Round | 1050 |
| Round | 1288 |
| Round | 1288 |
| Round | 1353 |
| Round | 1526 |
| Round | 1050 |
| Round | 1288 |
| Round | 1052 |
| Round | 1050 |
| Round | 1050 |
| Round | 1050 |
| Obround | 2119 |
| Obround | 1547 |
| Obround | 1640 |
| Obround | 2021 |
| Obround | 1482 |
| Obround | 1678 |
| Obround | 1915 |
| Obround | 2037 |
| Obround | 1581 |
| Obround | 1743 |
| Obround | 1783 |
| Obround | 1431 |
| Obround | 1567 |
| Obround | 1348 |
| Obround | 1447 |
| Obround | 1688 |
| Obround | 1674 |
| Obround | 2020 |

The average and standard deviation values for data recorded above are indicated in the table below:

|  | Round | Obround |
| --- | --- | --- |
| Average | 1061.778 | 1703.94444 |
| Stdev | 276.4375 | 232.924495 |
| Normalized Stdev | 26.03535 | 13.6697235 |

As noted in the above table, the normalized standard deviation (stdev) for obround was half of that for the round or circular shape (13.67% versus 26.04%). Since the obround shape conforms more easily to shape of part line between hairs on the head than small circles, separation of camera and hydration measuring area (as per our invention) permitted use of such obround shape and resulting hydration measurement which were less altered (i.e., less deviation).

In short, use of our device and use of oblong (especially obround) shape permits more accurate measurement of hydration (less deviation) which, in turn, permits better evaluation and ability to recommend.

The invention claimed is:

1. A device, comprising:
   a housing, containing a hydration meter, a camera and an electrical wire or cord for transmitting data and images,
   wherein the housing has a first projection, a second projection and a third projection, and a central gripping portion,
   wherein the first projection, the second projection, and the third projection extend radially from the central gripping portion,
   wherein the first projection is configured to contain the hydration meter at the terminus of the projection,
   wherein the hydration meter comprises a surface evaluation area having an aspect ratio from 1:1 to 20:1,
   wherein the hydration meter is configured to measure skin and/or hair hydration and capture data corresponding to the measured hydration data,
   wherein the second projection is configured to contain the camera at the terminus of the projection,
   wherein the camera is configured to capture images,
   wherein the third projection is configured to comprise the electrical wire or cord that is configured to transmit the data from the hydration meter and the images captured by the camera to a computer.

2. The device according to claim 1, wherein the aspect ratio is greater than or equal to 2:1.

3. The device according to claim 2, wherein the aspect ratio is greater than or equal to 3:1.

4. The device according to claim 1, wherein the surface evaluation area is in the shape of an ellipse and the width of the ellipse defines the major axis and the height of the ellipse defines the minor axis.

5. The device according to claim 4, wherein the aspect ratio is greater than or equal to 2:1.

6. The device according to claim 1, wherein the surface evaluation area is oblong in shape.

7. The device according to claim 6, wherein the oblong shape is a rectangle with rounded corners.

8. The device according to claim 1, wherein the surface evaluation area is obround in shape.

9. The device according to claim 1, where the images and data are stored in the computer.

10. The device according to claim 1, wherein the camera is in communication with a printed circuit board.

11. The device according to claim 1, further comprising light emitting diodes.

12. The device according to claim 11, wherein the diodes are positioned on a ring supporting the diodes.

13. The device according to claim 12, wherein there is also a diffuser and the diodes face the diffuser towards an opening of the housing on which the camera is supported.

14. The device according to claim 1, wherein the device communicates with the computer via a USB port.

15. The device according to claim 1, wherein the hydration meter comprises a transducer and an interface circuit which together measure capacitance.

16. The device according to claim 15, wherein a change in capacitance is used to measure hydration.

17. A method for recommending a particular consumer product for skin or hair to a consumer, comprising:
   obtaining data corresponding to the hydration of skin and capturing an image of at least one of the scalp or hair of a user, by applying the device of claim 1 on to the scalp of the consumer, transmitting the data and images to a computer preprogrammed with images, configured to compute, based on the data a hydration value, and based on the comparison of the captured images and the preprogrammed images, a score, and provide, based on the hydration value and score, a recommendation of a product.

* * * * *